United States Patent [19]
Dennis et al.

[11] Patent Number: 5,137,730
[45] Date of Patent: Aug. 11, 1992

[54] TABLET COMPOSITION AND METHOD FOR PROBLEM PHARMACEUTICAL MATERIALS USING CITRIC ACID

[75] Inventors: Andrew B. Dennis; Peter Timmins; Himadri Sen, all of Merseyside, United Kingdom

[73] Assignee: E. R. Squibb & Sons, Inc., Princeton, N.J.

[21] Appl. No.: 705,829

[22] Filed: May 28, 1991

Related U.S. Application Data

[63] Continuation-in-part of Ser. No. 512,726, Apr. 23, 1990, abandoned.

[51] Int. Cl.⁵ .................. A61K 9/14; A61K 9/20
[52] U.S. Cl. .................. 424/465; 424/464; 424/470; 424/489; 514/784; 514/960
[58] Field of Search .............. 424/465, 470, 466, 464

[56] References Cited

U.S. PATENT DOCUMENTS

| | | | |
|---|---|---|---|
| 4,808,413 | 2/1989 | Joshi et al. .................. | 424/458 |
| 4,942,039 | 7/1990 | Duvall et al. .................. | 424/466 |
| 4,950,484 | 8/1990 | Olthoff et al. .................. | 424/499 |

OTHER PUBLICATIONS

*Pharmaceutical Dosage Forms, Tablets*, vol. 1, 2nd Edition, pp. 188 and 189.
Botzolakis et al., Oct. 1988 AAPS meeting, PT 1691.
Kuhn et al., Oct. 1988 AAPS meeting, PT 1699.

*Primary Examiner*—Thurman K. Page
*Assistant Examiner*—James Spear
*Attorney, Agent, or Firm*—Theodore R. Furman, Jr.

[57] ABSTRACT

In accordance with the present invention an improved tablet composition for drugs or active ingredients prone to poor tabletting properties is disclosed. The improved composition comprises a premixture, consisting essentially of between about 85 and 99.9 percent by weight of the active ingredient and between about 0.1 and 15 percent by weight of citric acid, and one or more other formulation ingredients added to premixture. The present invention also involves the process for making such compositions and products therefrom.

15 Claims, 6 Drawing Sheets

TABLET COMPOSITION AND METHOD FOR PROBLEM PHARMACEUTICAL MATERIALS USING CITRIC ACID

This is a continuation-in-part of U.S. Ser. No. 512,726 filed Apr. 23, 1990, now abandoned.

BACKGROUND OF THE INVENTION

It is known that certain pharmacologically active ingredients are extremely difficult to manufacture in tablet form due to the physical nature of the active compound itself. For example, many drugs which when utilized in free base form, i.e., not in salt form, e.g. atenolol, nadolol, salbutamol, chlordiazepoxide, temazepam, diazepam, sulpiride, d-sotalol, d-L-sotalol and the like, are prone to many undesirable tabletting problems including poor compression and dissolution properties, high lubricant requirement, formation of soft granules and "sticking" which refers to the film-forming adherence phenomenon wherein the compound adheres to tablet punches and other manufacturing apparatus. These problems can result in soft tablets of high friability and tablets of inelegant appearance due to loss of material to punch surfaces. Attempting to reduce the compression problems by increasing compression forces in the tablet press can result in high disintegration times and slow drug release which may compromise bioavailability. In all instances so far discussed high ejection forces are needed to remove tablets from dies which can result in inelegant product and machine wear.

Increasing the level of certain excipient materials to compensate for these phenomena is not without difficulties. For example, increasing the level of hydrophobic tablet lubricants to reduce ejection forces and adhesion, e.g. magnesium stearate, decreases the attainable tablet hardness which in turn can result in poor handling properties and a decrease in the rate of drug release. Attempts to counter the decreased hardness with higher compression forces have given way to retardation of the tablet disintegration. Higher ratios of lubricant-to-drug can be provided without adversely affecting tablet hardness by proportionally increasing the levels of all of the other ingredients, except the drug itself. However, this results in a substantial increase in tablet size which is not at all desirable as this might compromise patient compliance.

SUMMARY OF THE INVENTION

In accordance with the present invention an improved tablet composition for drugs or active ingredients prone to adherence, etc., to tabletting apparatus is disclosed. The improved composition comprises a premixture, consisting essentially of between about 85 and 99.9 percent by weight of the active ingredient and between about 0.1 and 15 percent by weight of citric acid, and one or more other formulation ingredients added to the premixture. The present invention also involves the process for making such compositions and products therefrom.

DETAILED DESCRIPTION OF THE INVENTION

Figure 1:
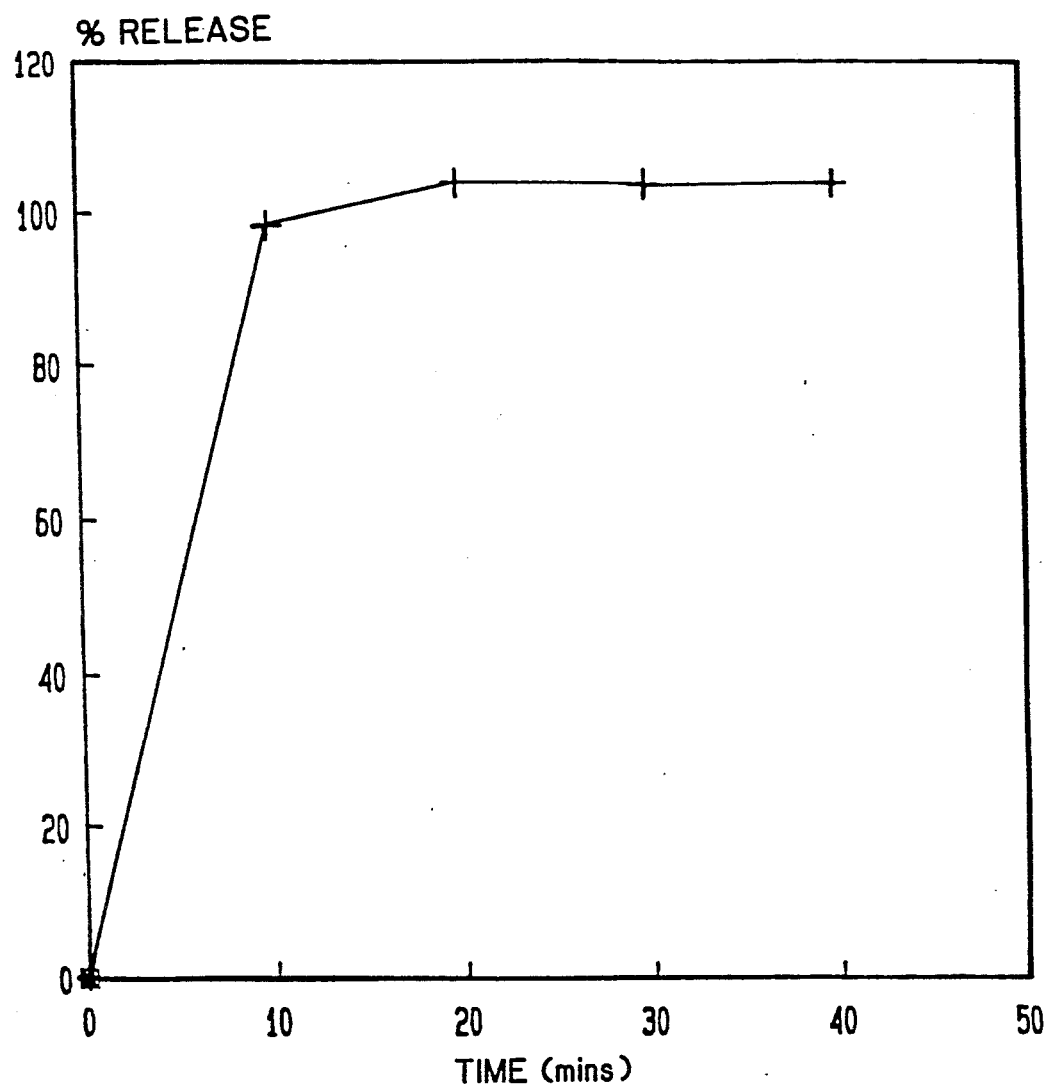
FIG. 1 shows the in vitro dissolution testing profile for atenolol tablets 100 mg prepared according to the proposed method.

In accordance with the present invention, large improvements in the handling/manufacturing of drugs, prone to compression, lubrication, sticking and adherence problems, into tablet form is provided. Not only does the present composition and process substantially eliminate these problems, but a smaller, more elegant dosage form having significantly enhanced disintegration and dissolution times is also provided.

As described above, the present composition is based upon granulating the active ingredient with citric acid prior to mixing with, and addition of, other formulation ingredients which may be desired and which are known in the art. The premixture preferably comprises about 85 to 99.9 percent by weight of the active ingredient and about 0.1 to 15 percent by weight of citric acid, and most preferably comprises a 92:8 to 99.5:0.5 ratio range of drug to citric acid. The citric acid, which is preferably in the form of an aqueous solution, and the active ingredient are mixed together, preferably by wet granulation. This premixture is then dried and thereafter mixed or blended with the one or more additional formulation ingredients. The so-formed material is then pressed into tablets by conventional means.

In trying to overcome the undesirable tabletting problems, it was found that a 4:1 ratio of drug to citric acid provided some alleviation of the problems as compared to formulations with no citric acid. However, the present compositions unexpectedly provide less adherence, improved compression, reduced ejection forces and more rapid disintegration and dissolution with less citric acid resulting in smaller tablet size. Further, the present composition allows for tablet sizes much smaller than those practicable for non-citric acid compositions which must employ larger proportions of all excipients so as to "swamp" the adherence problem, and to reduce problems of flow, compression, wetting, disintegration and dissolution. This may be of particular benefit for high dose drugs or in case of long term medications or in elderly patients where larger tablets could produce problems of patient compliance.

The present composition and method are suitable for any drug or active ingredient having one or more of the undesirable tabletting problems discussed above. Drugs known to possess such undesirable qualities, e.g. sticking, poor compression, high lubricant requirement, and the like, and to which the present invention has particular applicability, include basic drugs not commonly used as salts, such as nadolol, atenolol, salbutamol, chlordiazepoxide, temazepam, diazepam, sulpiride, d-sotalol or d-L-sotalol and the like. Preferred are compositions containing nadolol, atenolol, d-sotalol or d-L-sotalol.

As mentioned above, the citric acid, when premixed with the active ingredient, is preferably in aqueous solution. Solutions containing 5 percent to 50 percent of citric acid have been found useful and 20 percent citric acid solutions are preferred. Very high concentrations in solution present handling problems because of their viscosity.

The one or more additional formulation ingredients can be selected from a wide variety of ingredients known in the pharmaceutical formulation art. According to the desired properties of the tablet, any number of ingredients may be selected, alone or in combination, based upon their known uses in preparing tablet compositions. Such ingredients include, but are not limited to, diluents, compression aids, disintegrants, lubricants, binders, flavors, flavor enhancers, sweeteners and preservatives.

Preferred tablet compositions in accordance with the present invention comprise about up to 90 percent by weight of active ingredient; up to 7.5 percent by weight of citric acid; up to 95 percent of flow aid/filler/compression aid, for example microcrystalline cellulose or its mixtures with lactose, calcium phosphate and the like; up to 10 percent of disintegrant such as sodium starch glycollate, croscarmellose sodium, corn starch and the like; and, up to 2.0 percent by weight of one or more lubricants.

Most preferred tablet compositions in accordance with the present invention comprise about
28 percent by weight of atenolol or nadolol; 1.5 percent by weight of citric acid (anhydrous); 68.5 percent by weight of microcrystalline cellulose;
1 percent by weight of sodium starch glycollate; and
1 percent by weight of magnesium stearate.

A typical process in accordance with the present invention involves dissolving the citric acid in purified water to produce the desired (e.g., 20%) solution. A sufficient quantity of this solution is then added to the active ingredient and these are "pre-granulated" together in, for example, a planetary mixer and the resultant granules are dried.

The cricitcality of level of moisture following drying step is formulation dependent. Three percent is satisfactory for nadolol and atenolol products proposed. Higher levels can lead to sticking problems, at lower levels tablet compression may be impaired. The so-formed premixture is thereafter milled and blended with the remaining ingredients desired for the end product.

The present invention will be further described by reference to the Examples which follow. The invention is understood not to be limited to the details described therein.

EXAMPLE 1

Employing the ingredients listed below, tablets in accordance with the present invention were prepared as follows:

| Ingredient | Amount/tablet in mg |
|---|---|
| Atenolol (Active Ingredient) | 100.00 |
| Citric Acid (anhydrous) | 4.00 |
| Microcrystalline Cellulose (flow/compression aid and filler) | 169.00 |
| Sodium Starch Glycollate (disintegrant) | 3.00 |
| Magnesium Stearate (Lubricant) | 4.00 |

| Ingredient | Amount/tablet in mg |
|---|---|
| | 280.00 |

The citric acid was dissolved in purified water to provide a 20% citric acid solution. The atenolol was granulated with this solution in a planetary mixer and the resultant granules were dried in a tray dryer to less than 3 percent by weight loss on drying. The atenolol/citric acid premixture was hammer milled and blended with the other excipients. This material was compressed into 280 mg tablets. The resulting tablets showed excellent compression properties, with good hardness, rapid disintegration and low ejection residual areas, indicating little or no adherence problems. In vitro dissolution testing profile can be seen in FIG. 1.

EXAMPLE 2

Prior art atenolol formulation consisting of the following ingredients were prepared using standard techniques:

| Ingredient | mg/tablet |
|---|---|
| A. | |
| Atenolol | 50 mg |
| Avicel | 82 mg |
| Plasdone | 5 mg |
| Sodium Starch Glycollate | 2 mg |
| Magnesium Stearate | 1 mg |
| B. | |
| Atenolol | 50 mg |
| Lactose | 81 mg |
| Plasdone | 5 mg |
| Sodium Starch Glycollate | 2 mg |
| Magnesium Stearate | 2 mg |
| C. | |
| Atenolol | 50 mg |
| Lactose | 38.5 mg |
| Avicel | 38.5 mg |
| Plasdone | 5 mg |
| Sodium Starch Glycollate | 2 mg |
| Talc | 5 mg |
| Magnesium Stearate | 1 mg |

Table 1 shows a comparison of the physical properties of atenolol tablets in prior art vs. proposed formulations.

TABLE 1

Physical Properties of Atenolol Tablets

| | Proposed Formulation | Prior Art Formulation | | |
|---|---|---|---|---|
| | | a | b | c |
| Max. hardness attainable (scu) | 17.2 | 7.3 | 9.3 | 10.8 |
| Approx. disintegration time (mins) at target hardness (8 scu) | 0.75 | >15 | >15 | >15 |
| Friability % (at 8 scu) | 0.04 | — | — | — |
| Residual areas at target hardness | 4.5 | 13.9 | 25.0 | 5.2 |

EXAMPLE 3

Tablets in accordance with the present invention, containing nadolol instead of atenolol, were prepared as in Example 1 utilizing the ingredients below:

| Ingredient | mg/tablet |
|---|---|
| Nadolol | 80.0 mg |

-continued

| Ingredient | mg/tablet |
| --- | --- |
| Citric Acid Anhydrous | 4.0 mg |
| Avicel | 190.0 mg |
| Sodium Starch Glycollate | 3.0 mg |
| Magnesium Stearate | 3.0 mg |
| Total | 280.0 mg |

Also, prior art nadolol tablets were prepared as in Example 2 utilizing the ingredients below:

| Ingredient | mg/tablet |
| --- | --- |
| Nadolol | 80.00 mg |
| Citric Acid Anhydrous | 20.00 mg |
| Plasdone | 12.00 mg |
| Corn Starch | 186.66 mg |
| Avicel | 158.66 mg |
| Magnesium Stearate | 2.67 mg |
| Distilled Water | 23.33 ml* |
| Industrial Methylated Spirit | 70.00 ml* |
| Total | 460.00 mg |

*Removed during processing.

Figure 2:
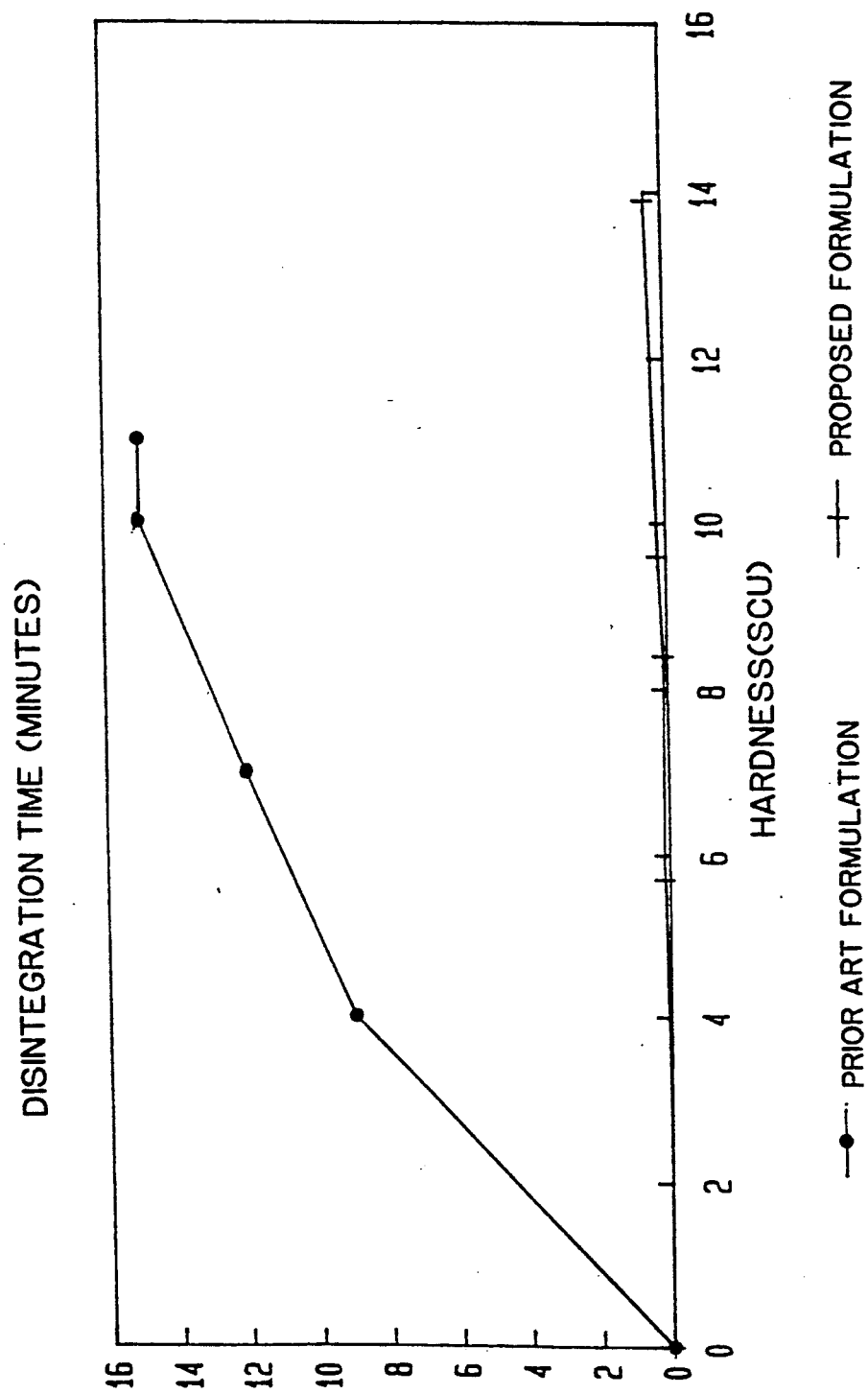
FIG. 2 shows the comparison of hardness-disintegration profiles for prior art vs. proposed nadolol tablet formulations.
Figure 3:
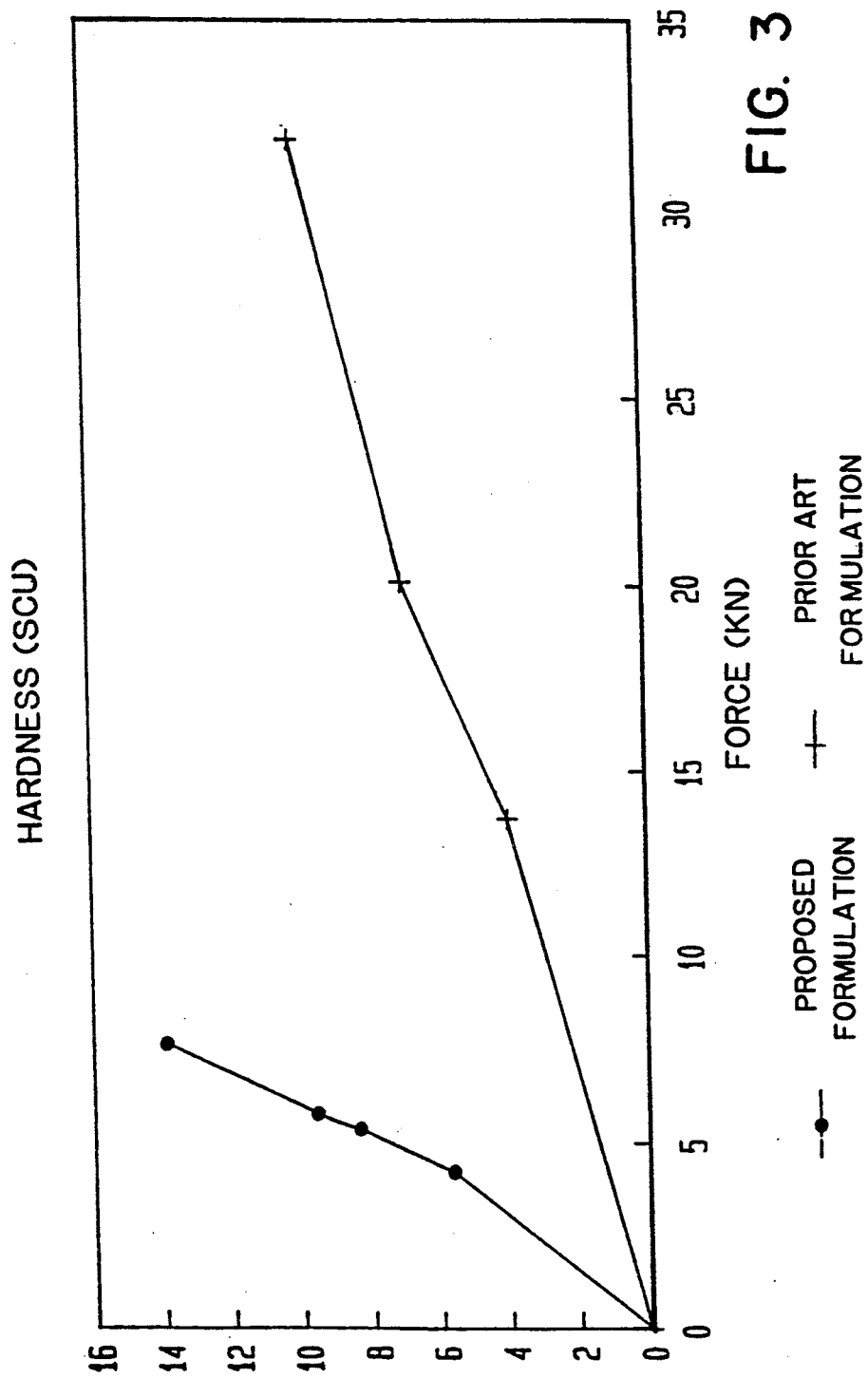
FIG. 3 shows the comparison of compression force-hardness profiles for prior art vs. proposed nadolol tablet formulations.
Figure 4:
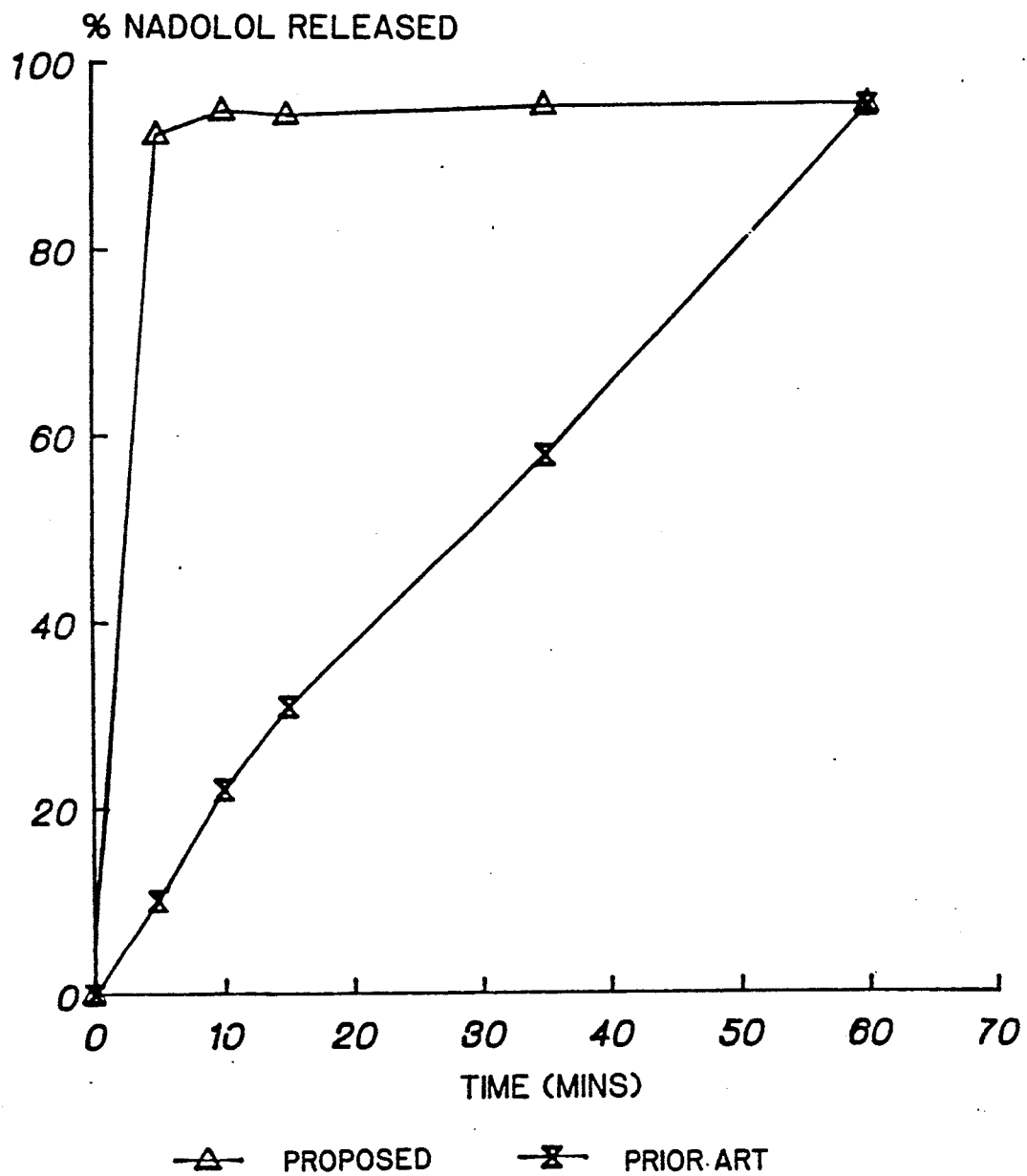
FIG. 4 shows comparison of in-vitro dissolution profiles of prior art and proposed nadolol formulations.
Figure 5:
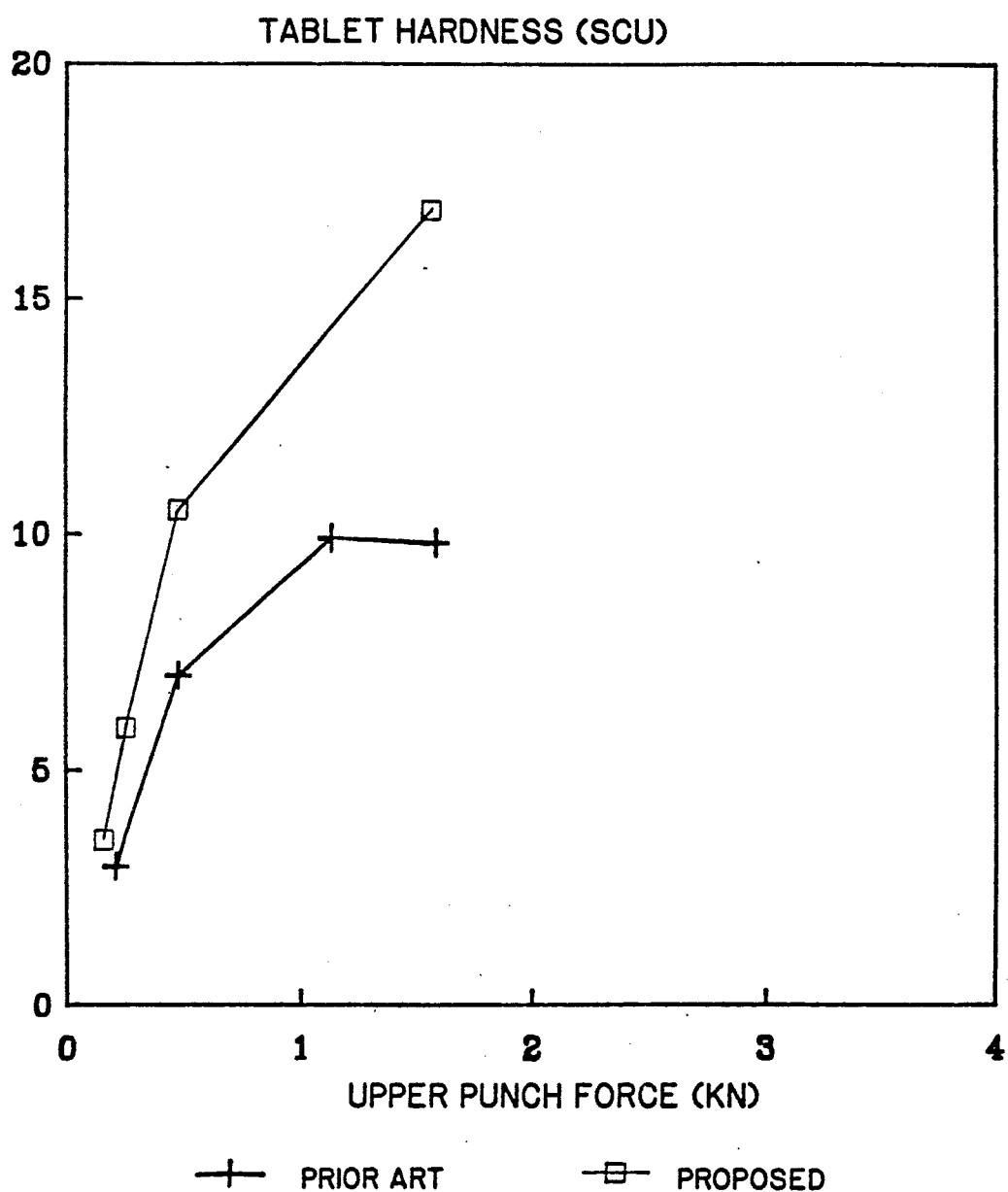
FIG. 5 shows compression force/hardness profiles for prior art and proposed atenolol tablet formulations.
Figure 6:
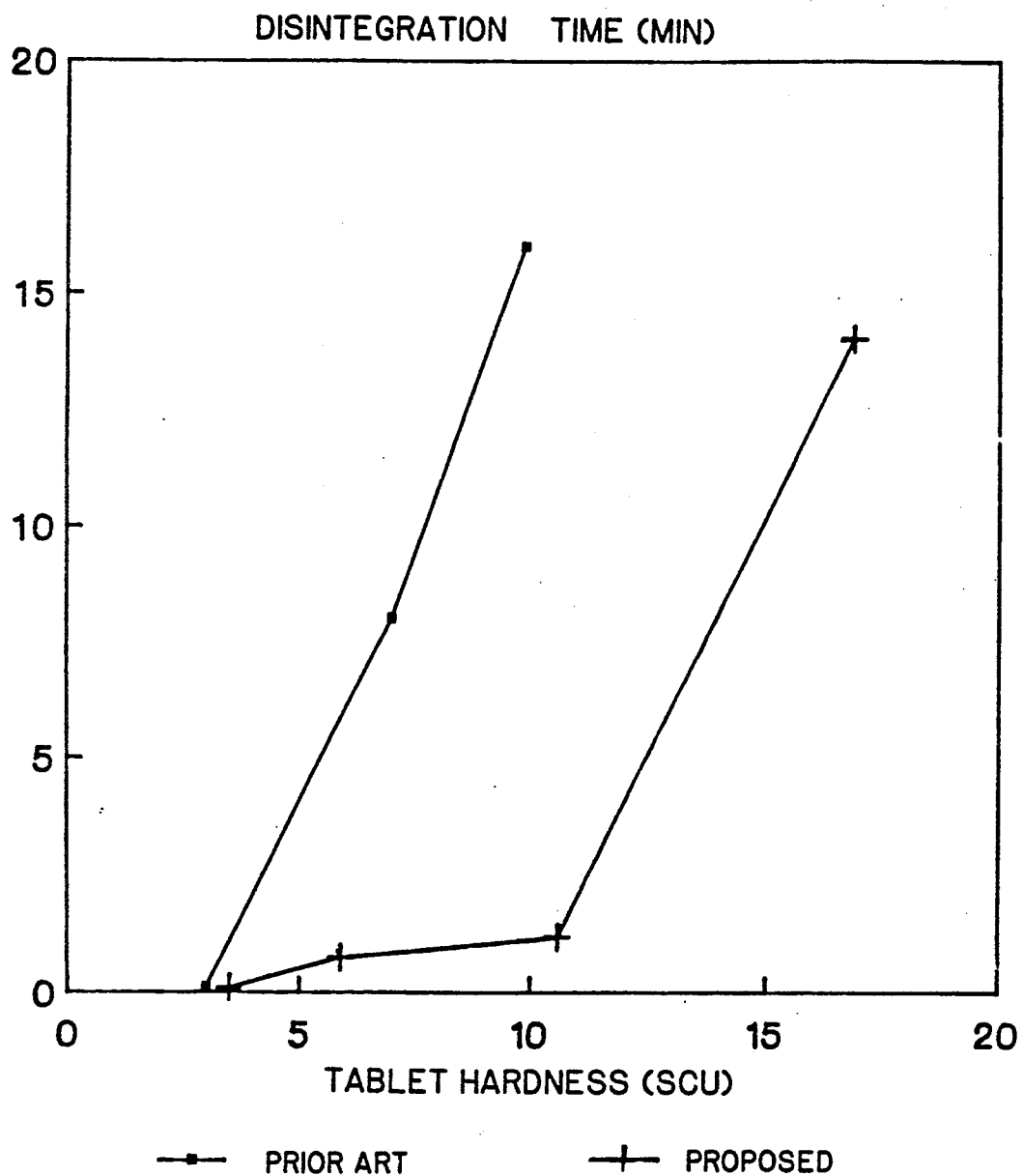
FIG. 6 shows comparative hardness/disintegration profiles between prior art and proposed atenolol tablet formulations.

Table 2 (below shows the physical properties of those nadolol tablets. It is seen that tablets of the present invention are smaller, have better disintegration times and better dissolution than the prior art tablets. FIGS. 2 and 3 illustrate the hardness-disintegration and compression force-hardness profiles, respectively, for the present and prior art nadolol compositions. FIG. 2 shows that the proposed nadolol compositions have excellent hardness while possessing much improved disintegration times. FIG. 3 shows that tablet hardness can be achieved with the proposed compositions with significantly less compression force.

TABLE 2

| Nadolol 80 mg Tablets Physical Properties | | |
| --- | --- | --- |
| | Prior Art Formulation | Proposed Formulation |
| Press weight | 455 mg | 280 mg |
| Disintegration time | 14 min. | <0.5 min. |
| % dissolution at 5 minutes | 10.2% | 92.0% |
| % dissolution at 10 minutes | 20.3% | 100.0% |
| % dissolution at 30 minutes | 57.5% | 100.0% |
| % dissolution at 60 minutes | 95.3% | 100.0% |

What is claimed is:

1. A process for preparing a tablet including an active ingredient selected from the group consisting of nadolol, atenolol, salbutamol, chlordiazepoxide, temazepam diazepam, sulpiride, d-sotalol and d-L-sotalol, which process comprises forming a premixture comprising from about 85 to about 99.9 percent by weight of said active ingredient and from about 0.1 to about 15 percent by weight of citric acid, by granulating said active ingredient and said citric acid together;

forming a final mixture by mixing the so formed granulated premixture with one or more additional formulation ingredients selected from the group consisting of diluents, compression aids, disintegrants, lubricants, binder, flavors, flavor enhancers, sweeteners and preservatives; and compressing the resultant final mixture into a desired tablet form.

2. The process of claim 1 wherein said premixture comprises about 96 percent by weight of said active ingredient and about 4 percent by weight of citric acid.

3. The process of claim 1 wherein said citric acid is in the form of an aqueous solution.

4. The process of claim 3 wherein said aqueous solution comprises about 5 to about 50 percent by weight of citric acid.

5. The process of claim 3 wherein said aqueous solution comprises about 20 percent by weight of citric acid.

6. The process of claim 1 wherein the pre-mixture is formed by wet granulation.

7. The process of claim 1 wherein said final mixture comprises from about 20 to about 50 percent by weight of premixture and from about 50 to about 80 percent by weight of other formulation ingredients.

8. The process of claim 1 wherein said final mixture comprises from about 35 to about 40 percent by weight of premixture and from about 60 to about 65 percent by weight of other formulation ingredients.

9. The process of claim 1 wherein said final mixture comprises from about 5 to about 90 percent by weight of active ingredient, from about 0.05 to about 13.5 percent by weight of citric acid, from about 0.1 to about 2.0 percent by weight of a lubricant, from about 0.5 to about 10 percent by weight of a disintegrant, and from about 5 to about 95 percent by weight of a filler which may also include flow aids and/or compression aids.

10. The process of claim 9 wherein said active ingredient is atenolol, nadolol, d-sotalol or d-L-sotalol.

11. The process of claim 9 wherein said lubricant is magnesium stearate.

12. The process of claim 9 wherein said disintegrant is selected from the group consisting of sodium starch glycollate, croscarmellose sodium and cornstarch.

13. The process of claim 9 wherein said filter with compression and/or flow aids is selected from the group consisting of microcrystalline cellulose and mixtures thereof with lactose and/or calcium phosphate.

14. The process of claim 9 wherein said final mixture comprises about 28 percent by weight of atenolol or nadolol; about 1.5 percent by weight of anhydrous citric acid; about 68.5 percent by weight of microcrystalline cellulose; about 1 percent by weight of sodium starch glycollate; and about 1 percent by weight of magnesium sterate.

15. A solid dosage form which includes an active ingredient selected from the group consisting of nadolol, atenolol, salbutamol chlordiazepoxide, temazepam, diazepam, sulpiride, d-sotalol and d-L-sotalol, wherein said dosage form is prepared by the process of claim 1.

* * * * *